(12) United States Patent
Lange

(10) Patent No.: US 11,464,457 B2
(45) Date of Patent: Oct. 11, 2022

(54) DETERMINING AN EARLY WARNING SCORE BASED ON WEARABLE DEVICE MEASUREMENTS

(71) Applicant: ChroniSense Medical Ltd., Yokneam (IL)

(72) Inventor: Daniel H. Lange, Kfar Vradim (IL)

(73) Assignee: ChroniSense Medical Ltd., Yokneam (IL)

( * ) Notice: Subject to any disclaimer, the term of this patent is extended or adjusted under 35 U.S.C. 154(b) by 81 days.

(21) Appl. No.: 15/854,628

(22) Filed: Dec. 26, 2017

(65) Prior Publication Data

US 2018/0132794 A1    May 17, 2018

Related U.S. Application Data

(63) Continuation-in-part of application No. 14/738,666, filed on Jun. 12, 2015, now Pat. No. 11,160,459, and
(Continued)

(51) Int. Cl.
*A61B 5/00* (2006.01)
*A61B 5/0205* (2006.01)
(Continued)

(52) U.S. Cl.
CPC ........ *A61B 5/7275* (2013.01); *A61B 5/02055* (2013.01); *A61B 5/14552* (2013.01);
(Continued)

(58) Field of Classification Search
CPC .............. A61B 5/7275; A61B 5/02055; A61B 5/14552; A61B 5/4035; A61B 5/681;
(Continued)

(56) References Cited

U.S. PATENT DOCUMENTS

| 3,885,552 A | 5/1975 | Kennedy |
| 3,898,984 A | 8/1975 | Mandel et al. |

(Continued)

FOREIGN PATENT DOCUMENTS

| CN | 1335756 A | 2/2002 |
| CN | 106901747 A | 6/2017 |

(Continued)

OTHER PUBLICATIONS

Arza et al., "Pulse Transit Time and Pulse Width as Potential Measure for estimating Beat-to-Beat Systolic and Diastolic Blood Pressure", Computing in Cardiology 2013, pp. 887-890.
(Continued)

*Primary Examiner* — Lynsey C Eiseman
*Assistant Examiner* — Jessandra F Hough
(74) *Attorney, Agent, or Firm* — Carr & Ferrell LLP

(57) ABSTRACT

A method and systems for determining an early warning score for a health status of a patient are provided. An example method includes acquiring, during a predetermined time period via sensors integrated into a wearable device worn on a wrist of the patient, initial values of medical parameters of patient. The medical parameters include a respiratory rate, oxygen saturation, temperature, blood pressure, and pulse rate, and level of consciousness. The method includes determining, based on the initial values, normal values of the medical parameters. The method includes acquiring, via the sensors and at a pre-determined frequency, further values of the medical parameters. The method includes determining, based on deviations of the further values from the normal values, individual scores for the medical parameters. The method includes calculating, based on the individual scores, a general score. The method includes determining, based on the general score, the health status of the patient.

24 Claims, 7 Drawing Sheets

Related U.S. Application Data a continuation-in-part of application No. 14/738,636, filed on Jun. 12, 2015, and a continuation-in-part of application No. 14/738,711, filed on Jun. 12, 2015, now Pat. No. 10,470,692.

(51) Int. Cl.

| | | |
|---|---|---|
| *A61B 5/1455* | (2006.01) | |
| *G16H 40/67* | (2018.01) | |
| *G16H 50/20* | (2018.01) | |
| *G16H 50/30* | (2018.01) | |
| *G16H 40/63* | (2018.01) | |
| *A61B 5/024* | (2006.01) | |
| *A61B 5/08* | (2006.01) | |
| *A61B 5/021* | (2006.01) | |
| *A61B 5/349* | (2021.01) | |

(52) U.S. Cl.
CPC ............ *A61B 5/4035* (2013.01); *A61B 5/681* (2013.01); *A61B 5/746* (2013.01); *G16H 40/63* (2018.01); *G16H 40/67* (2018.01); *G16H 50/20* (2018.01); *G16H 50/30* (2018.01); *A61B 5/0022* (2013.01); *A61B 5/021* (2013.01); *A61B 5/024* (2013.01); *A61B 5/02427* (2013.01); *A61B 5/0816* (2013.01); *A61B 5/349* (2021.01)

(58) Field of Classification Search
CPC ....... A61B 5/746; A61B 5/0022; A61B 5/021; A61B 5/024; A61B 5/02427; A61B 5/0452; A61B 5/0816
See application file for complete search history.

(56) References Cited

U.S. PATENT DOCUMENTS

| | | | |
|---|---|---|---|
| 4,331,154 A | 5/1982 | Broadwater et al. | |
| 4,732,158 A | 3/1988 | Sadeh | |
| 4,802,486 A | 2/1989 | Goodman et al. | |
| 5,050,612 A * | 9/1991 | Matsumura | A61M 5/14248 600/483 |
| 5,316,008 A | 5/1994 | Suga et al. | |
| 5,503,148 A | 4/1996 | Pologe et al. | |
| 5,692,505 A | 12/1997 | Fouts | |
| 5,935,060 A | 8/1999 | Iliff | |
| 6,047,203 A | 4/2000 | Sackner et al. | |
| 6,139,494 A | 10/2000 | Cairnes | |
| 6,527,725 B1 | 3/2003 | Inukai et al. | |
| 7,184,809 B1 | 2/2007 | Sterling et al. | |
| 7,479,111 B2 | 1/2009 | Zhang et al. | |
| 7,544,168 B2 | 6/2009 | Nitzan | |
| 7,738,935 B1 | 6/2010 | Turcott | |
| 8,172,764 B2 | 5/2012 | Gregson et al. | |
| 8,602,997 B2 | 12/2013 | Banet et al. | |
| 8,866,606 B1 | 10/2014 | Will et al. | |
| 10,470,692 B2 | 11/2019 | Lange et al. | |
| 10,687,742 B2 | 6/2020 | Lange et al. | |
| 10,952,638 B2 | 3/2021 | Lange | |
| 11,000,235 B2 | 5/2021 | Lange | |
| 11,160,459 B2 | 11/2021 | Gross et al. | |
| 11,160,461 B2 | 11/2021 | Lange | |
| 2001/0005773 A1 | 6/2001 | Larsen et al. | |
| 2001/0029326 A1 | 10/2001 | Diab et al. | |
| 2002/0095077 A1 | 7/2002 | Swedlow et al. | |
| 2002/0133068 A1 | 9/2002 | Huiku | |
| 2003/0009091 A1 | 1/2003 | Edgar, Jr. et al. | |
| 2003/0036685 A1 | 2/2003 | Goodman | |
| 2003/0065269 A1 | 4/2003 | Vetter et al. | |
| 2003/0109776 A1 | 6/2003 | Jacques | |
| 2003/0139654 A1 | 7/2003 | Kim et al. | |
| 2003/0163033 A1 | 8/2003 | Dekker | |
| 2004/0215095 A1 | 10/2004 | Lee et al. | |
| 2005/0070775 A1 | 3/2005 | Chin et al. | |
| 2005/0215913 A1 | 9/2005 | Lee et al. | |
| 2005/0281439 A1 | 12/2005 | Lange | |
| 2006/0074322 A1 | 4/2006 | Nitzan | |
| 2006/0241510 A1 | 10/2006 | Halperin | |
| 2006/0264767 A1 | 11/2006 | Shennib | |
| 2007/0142720 A1 | 6/2007 | Ridder et al. | |
| 2007/0191725 A1 | 8/2007 | Nelson | |
| 2008/0146954 A1 | 6/2008 | Bojovic et al. | |
| 2008/0208069 A1 | 8/2008 | John et al. | |
| 2008/0214961 A1 | 9/2008 | Matsumoto et al. | |
| 2008/0221419 A1 | 9/2008 | Furman | |
| 2008/0255433 A1 | 10/2008 | Prough et al. | |
| 2009/0024011 A1 | 1/2009 | Huiku | |
| 2009/0163821 A1 | 6/2009 | Sola I Caros et al. | |
| 2009/0247848 A1 | 10/2009 | Baker, Jr. | |
| 2010/0016694 A1 | 1/2010 | Martin et al. | |
| 2010/0179438 A1 | 7/2010 | Heneghan et al. | |
| 2010/0192952 A1 | 8/2010 | Melker et al. | |
| 2010/0217144 A1 | 8/2010 | Brian | |
| 2010/0298656 A1 | 11/2010 | McCombie et al. | |
| 2010/0312079 A1 | 12/2010 | Larsen et al. | |
| 2010/0324384 A1 | 12/2010 | Moon et al. | |
| 2011/0060200 A1 | 3/2011 | Bernreuter | |
| 2011/0066051 A1 | 3/2011 | Moon et al. | |
| 2011/0077486 A1 | 3/2011 | Watson et al. | |
| 2011/0082355 A1 | 4/2011 | Eisen et al. | |
| 2011/0201946 A1 | 8/2011 | Turcott | |
| 2011/0224564 A1 | 9/2011 | Moon et al. | |
| 2011/0257551 A1 | 10/2011 | Banet et al. | |
| 2012/0190944 A1 | 7/2012 | Thaveeprungsriporn et al. | |
| 2012/0238834 A1 | 9/2012 | Hornick | |
| 2013/0231947 A1 | 9/2013 | Shusterman | |
| 2013/0296665 A1 | 11/2013 | Kassim et al. | |
| 2013/0296666 A1 | 11/2013 | Kumar et al. | |
| 2013/0296673 A1 | 11/2013 | Thaveeprungsriporn et al. | |
| 2013/0310700 A1 | 11/2013 | Wiard et al. | |
| 2013/0338460 A1 | 12/2013 | He et al. | |
| 2014/0043164 A1 | 2/2014 | Eschelman et al. | |
| 2014/0088449 A1 | 3/2014 | Nearing et al. | |
| 2014/0142445 A1 | 5/2014 | Banet et al. | |
| 2014/0142456 A1* | 5/2014 | Fischer | A61B 5/091 600/538 |
| 2014/0155705 A1 | 6/2014 | Papadopoulos et al. | |
| 2014/0206948 A1 | 7/2014 | Romem | |
| 2014/0257122 A1* | 9/2014 | Ong | A61B 5/02405 600/515 |
| 2014/0275888 A1 | 9/2014 | Wegerich et al. | |
| 2014/0278229 A1* | 9/2014 | Hong | A63B 71/06 702/160 |
| 2015/0109125 A1 | 4/2015 | Kaib et al. | |
| 2015/0148622 A1 | 5/2015 | Moyer et al. | |
| 2015/0157220 A1 | 6/2015 | Fish et al. | |
| 2015/0157262 A1 | 7/2015 | Schuessler | |
| 2015/0196257 A1 | 7/2015 | Yousefi et al. | |
| 2015/0265161 A1 | 9/2015 | Hernandez et al. | |
| 2015/0272510 A1* | 10/2015 | Chin | A61B 5/7275 600/515 |
| 2015/0305689 A1* | 10/2015 | Gourmelon | A61B 5/002 600/301 |
| 2015/0313484 A1 | 11/2015 | Burg et al. | |
| 2015/0320328 A1 | 11/2015 | Albert | |
| 2015/0332012 A1 | 11/2015 | Edelson et al. | |
| 2015/0342538 A1* | 12/2015 | St. Pierre | A61B 5/7275 600/301 |
| 2015/0366469 A1 | 12/2015 | Harris et al. | |
| 2015/0366492 A1 | 12/2015 | Haan et al. | |
| 2015/0366518 A1 | 12/2015 | Sampson | |
| 2016/0000376 A1* | 1/2016 | Murray | A61B 5/6833 600/534 |
| 2016/0007935 A1 | 1/2016 | Hernandez et al. | |
| 2016/0022220 A1 | 1/2016 | Lee et al. | |
| 2016/0089033 A1 | 3/2016 | Saponas et al. | |
| 2016/0093205 A1* | 3/2016 | Boyer | A61B 5/02416 340/506 |
| 2016/0120434 A1 | 5/2016 | Park et al. | |
| 2016/0183846 A1 | 6/2016 | Derkx | |
| 2016/0270668 A1 | 9/2016 | Gil | |
| 2016/0270677 A1 | 9/2016 | Lin | |

(56) References Cited

U.S. PATENT DOCUMENTS

| | | | |
|---|---|---|---|
| 2016/0360971 | A1 | 12/2016 | Gross et al. |
| 2016/0360974 | A1 | 12/2016 | Lange |
| 2016/0360986 | A1 | 12/2016 | Lange |
| 2016/0361003 | A1 | 12/2016 | Lange et al. |
| 2016/0361004 | A1 | 12/2016 | Lange et al. |
| 2017/0014037 | A1 | 1/2017 | Coppola et al. |
| 2017/0156593 | A1 | 6/2017 | Ferber et al. |
| 2017/0202459 | A1 | 7/2017 | Cao |
| 2017/0258406 | A1 | 9/2017 | Lange |
| 2018/0098705 | A1 | 4/2018 | Chaturvedi et al. |
| 2018/0247713 | A1 | 8/2018 | Rothman |
| 2019/0015014 | A1 | 1/2019 | Lange |
| 2021/0145310 | A1 | 5/2021 | Lange |
| 2021/0401313 | A1 | 12/2021 | Lange |

FOREIGN PATENT DOCUMENTS

| | | |
|---|---|---|
| CN | 107920786 A | 4/2018 |
| CN | 107920786 B | 12/2020 |
| EP | 2430975 A1 | 3/2012 |
| EP | 3307146 A1 | 4/2018 |
| EP | 3307150 A1 | 4/2018 |
| EP | 3307162 A1 | 4/2018 |
| EP | 3493734 A1 | 6/2019 |
| EP | 3307146 B1 | 11/2020 |
| EP | 3731744 A1 | 11/2020 |
| EP | 3849407 A1 | 7/2021 |
| EP | 3493734 B1 | 9/2021 |
| EP | 3307162 B1 | 11/2021 |
| WO | WO0047108 A1 | 8/2000 |
| WO | WO2001015597 A1 | 3/2001 |
| WO | WO2006048701 A2 | 5/2006 |
| WO | WO2013061415 A1 | 5/2013 |
| WO | WO2014022906 A1 | 2/2014 |
| WO | WO2015047015 A1 | 4/2015 |
| WO | WO2015070030 A1 | 5/2015 |
| WO | WO2015197383 A1 | 12/2015 |
| WO | WO2016110804 A1 | 7/2016 |
| WO | WO2016199121 A1 | 12/2016 |
| WO | WO2016199122 A1 | 12/2016 |
| WO | WO2016199123 A1 | 12/2016 |
| WO | WO2016199124 A1 | 12/2016 |
| WO | WO2017079828 A1 | 5/2017 |
| WO | WO2017140696 A1 | 8/2017 |
| WO | WO2017141131 A1 | 8/2017 |
| WO | WO2017158585 A1 | 9/2017 |
| WO | WO2018025257 A1 | 2/2018 |
| WO | WO2018085563 A1 | 5/2018 |
| WO | WO2019130296 A1 | 7/2019 |
| WO | WO2020053858 A1 | 3/2020 |

OTHER PUBLICATIONS

Ye et al., "Estimation of Systolic and Diastolic Pressure using the Pulse Transit Time", International Journal of Medical, Health, Biomedical, Bioengineering and Pharmaceutical Engineering vol. 4. No. 7, 2010, pp. 303-308.

International Search Report and Written Opinion dated Jul. 11, 2016 in Patent Cooperation Treaty Application No. PCT/IL2016/050511 filed May 15, 2016, 19 pages.

International Search Report and Written Opinion dated Aug. 18, 2016 in Patent Cooperation Treaty Application No. PCT/IL2016/050514 filed May 15, 2016, 20 pages.

International Search Report and Written Opinion dated Aug. 29, 2016 in Patent Cooperation Treaty Application No. PCT/IL2016/050513 filed May 15, 2016, 18 pages.

Patent Cooperation Treaty Application No. PCT/IL2016/050512, "International Search Report" and "Written Opinion of the International Searching Authority," Sep. 18, 2016, 9 pages.

"International Search Report" and "Written Opinion of the International Searching Authority," Patent Cooperation Treaty Application No. PCT/IL2017/050242, dated Jun. 13, 2017, 12 pages.

Abtahi, Farhad, "Feasibility of Fetal EEG Recording," Master's Thesis, Department of Signal and System, Chalmers University of Technology, Gothenburg, Sweden, Jan. 1, 2011, 51 pages.

Richardson, Kelly et al., "Electrocardiographic damage scores and cardiovascular mortality," American Heart Journal vol. 149, No. 3, Mar. 1, 2005, pp. 458-463.

"International Search Report" and "Written Opinion of the International Searching Authority," Patent Cooperation Treaty Application No. PCT/IL2017/050826, dated Oct. 23, 2017, 9 pages.

"Extended European Search Report," European Patent Application No. 17836517.7, dated Feb. 25, 2020, 5 pages.

"Office Action," Chinese Patent Application No. 201680042023.6, dated Mar. 20, 2020, 10 pages.

"Office Action," European Patent Application No. 16807013.4, dated Aug. 27, 2019, 6 pages.

"International Search Report" and "Written Opinion of the International Searching Authority," Patent Cooperation Treaty Application No. PCT/IL2019/051018, dated Dec. 17, 2019, 14 pages.

"Notice of Allowance," European Patent Application No. 16807013.4, dated May 26, 2020, 7 pages.

"Office Action," European Patent Application No. 16807015.9, dated Aug. 6, 2020, 7 pages.

"Extended European Search Report," European Patent Application No. 16807014.2, dated Oct. 22, 2018, 8 pages.

"Extended European Search Report," European Patent Application No. 16807015.9, dated Jan. 21, 2019, 10 pages.

Gözde, Ateşet al., "Measuring of Oxygen Saturation Using Pulse Oximeter Based on Fuzzy Logic," Medical Measurements and Applications Proceedings (MEMEA), 2012 IEEE International Symposium, May 18, 2012, pp. 1-6.

"Extended European Search Report," European Patent Application No. 16807013.4, dated Jan. 17, 2019, 7 pages.

"International Search Report" and "Written Opinion of the International Searching Authority," Patent Cooperation Treaty Application No. PCT/IL2018/051384, dated Mar. 14, 2019, 15 pages.

"Notice of Allowance", European Patent Application No. 17836517.7, dated Oct. 1, 2020, 7 pages.

"Notice of Allowance", European Patent Application No. 16807015.9, dated Mar. 9, 2021, 7 pages.

"Office Action", European Patent Application No. 16807014.2, dated Apr. 30, 2021, 6 pages.

Sam et al., "Feasibility of single-arm single-lead ECG biometrics", 22nd European Signal Processing Conference (EUSIPCO), Sep. 1, 2014, pp. 2525-2529.

"Extended European Search Report", European Patent Application No. 18897389.5, dated Aug. 4, 2021, 9 pages.

Zhang et al., "Theoretical Study on the Effect of Sensor Contact Force on Pulse Transmit Time", IEEE Transactions on Biomedical Engineering, Sep. 2007, 10 pages.

\* cited by examiner

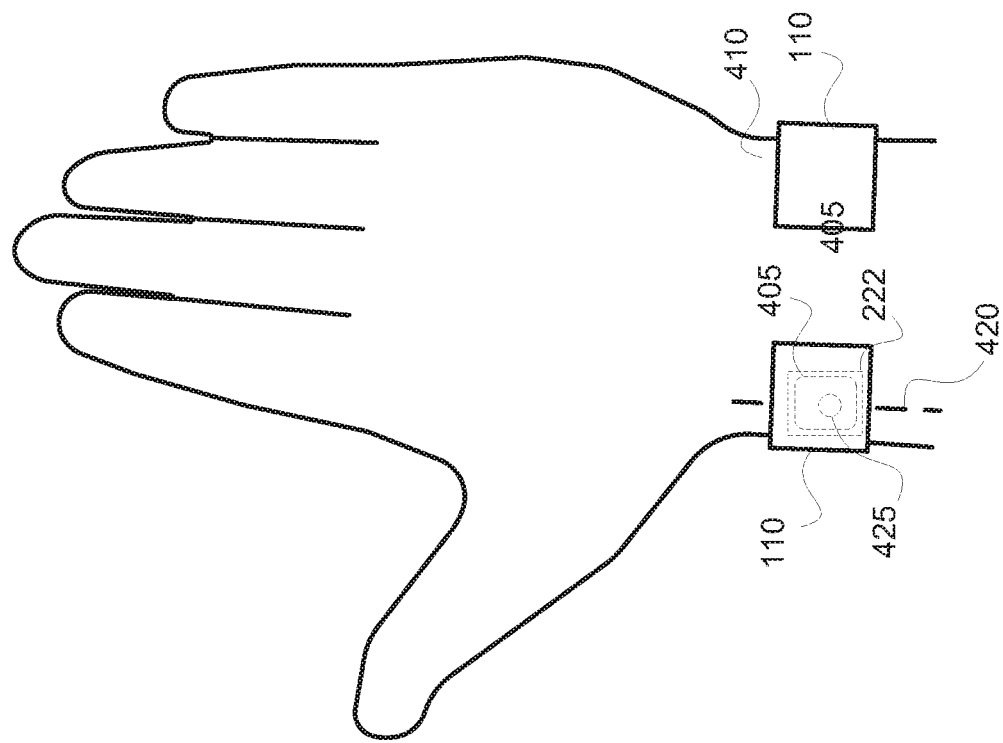
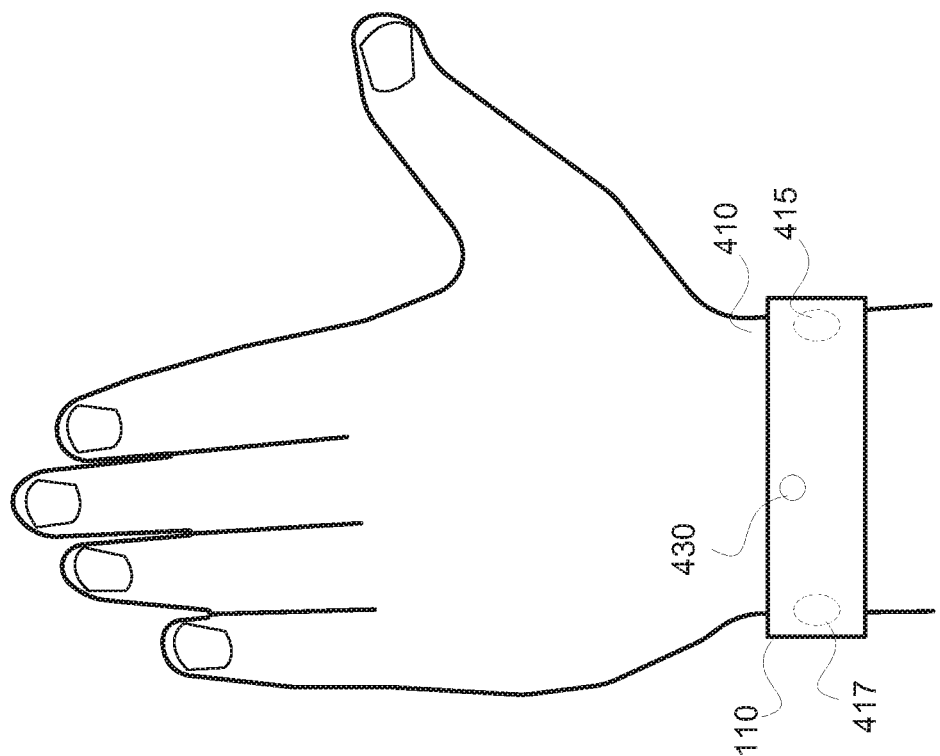

DETERMINING AN EARLY WARNING SCORE BASED ON WEARABLE DEVICE MEASUREMENTS

CROSS-REFERENCE TO RELATED APPLICATIONS

The present application is a Continuation-in-Part of U.S. patent application Ser. No. 14/738,666, titled "Monitoring Health Status of People Suffering from Chronic Diseases", filed on Jun. 12, 2015, a Continuation-in-Part of U.S. patent application Ser. No. 14/738,636, titled "Wearable Device Electrocardiogram", filed on Jun. 12, 2015, and a Continuation-in-Part of U.S. patent application Ser. No. 14/738,711, titled "System for Performing Pulse Oximetry", filed on Jun. 12, 2015. The disclosures of the aforementioned applications are incorporated herein by reference for all purposes, including all references cited therein.

FIELD

The present application relates to systems and methods for monitoring health status of people, and more specifically systems and method for determining an early warning score (EWS) based on wearable device measurements.

BACKGROUND

It should not be assumed that any of the approaches described in this section qualify as prior art merely by virtue of their inclusion in this section.

Monitoring health status of a patient and progression of chronic diseases, which includes measuring medical parameters, is central for providing appropriate and timely treatment to patients suffering from such chronic diseases as chronic heart failure, cardiac arrhythmia, chronic obstructive pulmonary disease, asthma, and diabetes. Recently, an EWS technique was introduced to facilitate estimation of a degree of illness of a patient. The EWS can be determined based on medical parameters, such as a respiratory rate, oxygen saturation, temperature, blood pressure, pulse rate, and level consciousness. Traditionally, monitoring is carried out and measurements are taken while a patient is hospitalized or in other clinical settings. Appropriate treatment regimen can be based on these measurements, and thus it is highly beneficial to monitor medical parameters of the patient after the patient is released from the hospital. Therefore, the patient can be asked to visit the hospital or clinic periodically for monitoring, and adjustment of treatment, if necessary. However, most often, no measurements are carried out between visits, usually due to the need for trained examiners and medical devices. This is unfortunate, because between visits the chronic disease from which the patient suffers can worsen and result in emergency treatment and hospitalization. Furthermore, after receiving repeated courses of emergency hospital treatment, the patient's health condition may degrade and never return to the pre-hospitalization level. Therefore, a technology that allows for at-home measurements can be essential to managing chronic diseases or even saving a patient's life. Early warnings of worsening conditions associated with chronic diseases may prevent unnecessary hospitalizations by providing a preventive treatment and, as a result, reduce financial and human costs of the hospitalization and treatment.

Currently there are no user-friendly devices for continuous non-intrusive measurements of medical parameters of patients at their home or working environment. In some cases, patients with severe symptoms can be monitored at home while staying in bed. However, devices for taking measurements of bedridden patients are generally not suitable for chronic patients which, with timely treatment, should be able to maintain a high quality normal life.

Some existing mobile devices can provide functionalities for tracking people's physical activity. Such devices can measure a pulse rate and the distance a person walks or runs, calculate burned calories, and so forth. Some of these existing devices are designed as or are part of a watch, a bracelet, and a wristband. However, these devices are primarily designed for healthy people for monitoring of their physical exercise and not for monitoring health status of people.

SUMMARY

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

According to one embodiment of the present disclosure, a system for providing an EWS for a health status of a patient is provided. The system may include a set of sensors configured to continuously collect a plurality of medical parameters of the patient. The sensors can be integrated into a wearable device. The wearable device can be designed to be worn on a wrist of the patient. The system may further include at least one processor communicatively coupled to the sensors. The at least one processor can be configured to acquire, via the sensors and during a predetermined time period, initial values of the medical parameters. The at least one processor can be further configured to determine, based on the initial values, normal values of the medical parameters. The at least one processor can be further configured to acquire, via the sensors and at a pre-determined frequency, further values of the medical parameters. The at least one processor can be further configured to determine, based on deviations of the further values from the normal values, individual scores for the medical parameters. The at least one processor can be further configured to calculate, based on the individual scores, a general score. The at least one processor can be further configured to determine, based at least on the general score, a health status of the patient.

In some embodiments, determining the individual scores includes selecting decimal numbers assigned to pre-determined ranges of the medical parameters. In certain embodiments, the decimal numbers and the pre-determined ranges can be based on a gender, an age, an ethnicity, a gene expression, and environmental conditions of the patient.

In some embodiments, determining the general score includes summation of the individual scores.

In some embodiments, the individual scores are multiplied by pre-defined weights prior to summations, the weights being based on one of a previous health status of the patient and environmental conditions of the patient.

In some embodiments, the at least one processor is further configured to adjust, based on the general score, the pre-determined frequency of acquiring the further values of the medical parameters.

In some embodiments, the at least one processor is further configured to determine that the general score exceed a first pre-determined threshold. If the result of the determination is positive, the at least one processor is further configured to issue an alarm regarding the health status of the patient.

In some embodiments, the medical parameters include at least a respiratory rate, an oxygen saturation, a temperature, a systolic blood pressure, and a pulse rate.

In some embodiments, the medical parameters further include a level of consciousness. In certain embodiments, the wearable device may include an alarm unit and a touch sensor. The alarm unit and the touch sensor can be communicatively coupled to the at least one processor. The at least one processor can be further configured to enable the alarm unit to prompt the patient to touch the touch sensor on the wearable device. The at least one processor can be further configured to determine, via the touch sensor, whether the patient touched the touch sensor. Based on the result of the determination, the at least one processor can be further configured to evaluate the level of consciousness.

In some embodiments, the wearable device may include at least one gyroscope configured to provide motion data. The at least one processor can be further configured to analyze the motion data to obtain a spectrum and determine, based on the spectrum, the respiratory rate.

In some embodiments, the wearable device may include at least one temperature sensor. The temperature sensor can be configured to measure the temperature from a skin area covering a radial artery.

According to another embodiment of the present disclosure, a method for providing an EWS for a health status of a patient is disclosed. The method can include acquiring, during a predetermined time period, by at least one processor communicatively coupled to sensors integrated into a wearable device, initial values of medical parameters of patient. The wearable device can be designed to be worn on a wrist of the patient. The method may include determining, by the at least one processor and based on the initial values, normal values of the medical parameters. The method may further include acquiring, by the at least one processor via the sensors and at a pre-determined frequency, further values of the medical parameters. The method may further allow determining, by the at least one processor and based on deviations of the further values from the normal values, individual scores for the medical parameters. The method may further include calculating, by the at least one processor and based on the individual scores, a general score. The method may further include determining, by the at least one processor and based at least on the general score, the health status of the patient.

According to another example embodiment of the present disclosure, the steps of the method for providing an EWS for a health status of a patient are stored on a non-transitory machine-readable medium comprising instructions, which when implemented by one or more processors perform the recited steps.

Other example embodiments of the disclosure and aspects will become apparent from the following description taken in conjunction with the following drawings.

BRIEF DESCRIPTION OF THE DRAWINGS

Embodiments are illustrated by way of example and not limitation in the figures of the accompanying drawings, in which like references indicate similar elements and in which:

FIGS. 4A and 4B are schematic diagrams illustrating an example device for providing EWS for a health status of a patient.

DETAILED DESCRIPTION

Figure 1:
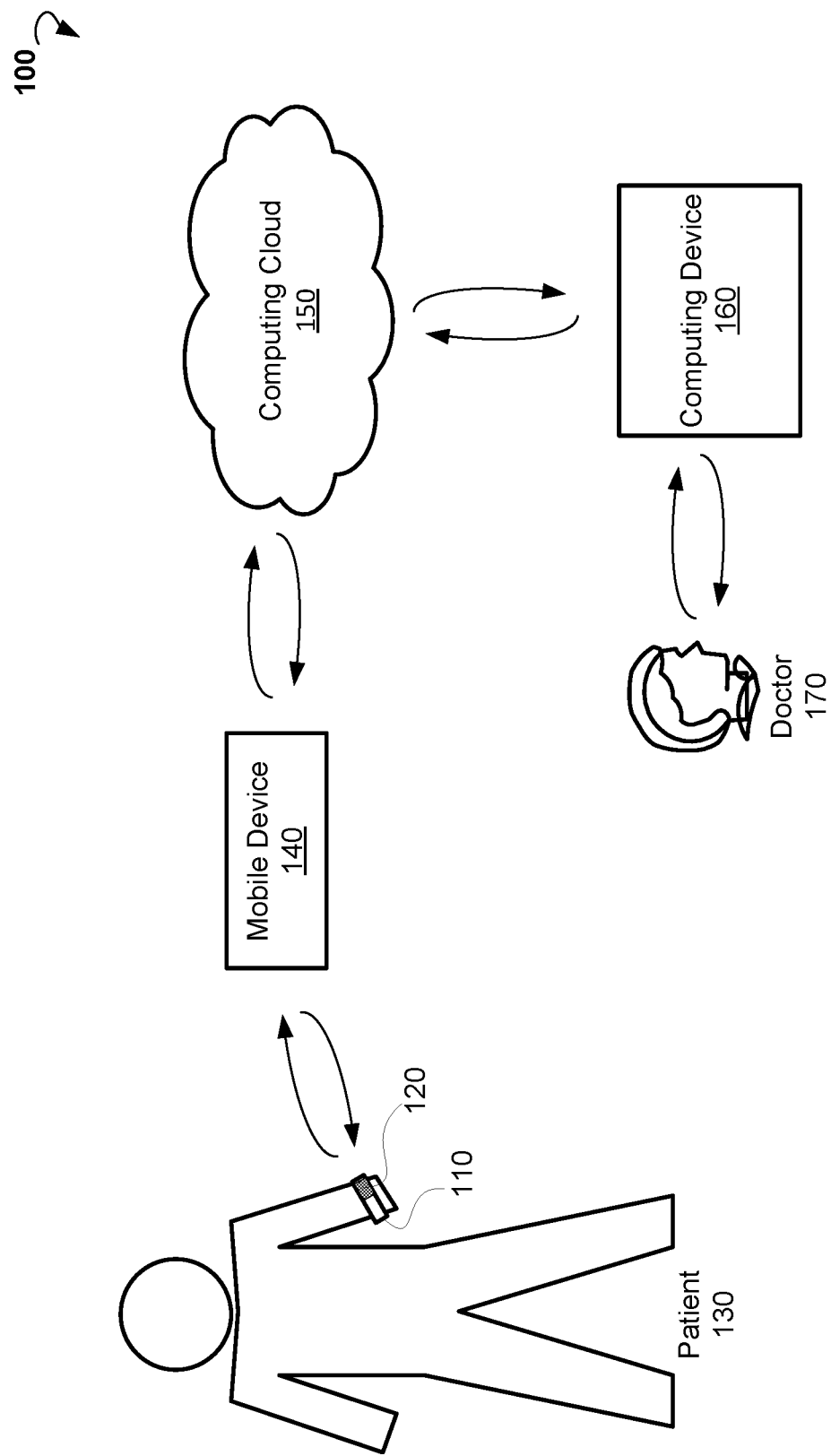
FIG. 1 is a block diagram showing an example system for providing EWS for a health status of a patient.

The following detailed description includes references to the accompanying drawings, which form a part of the detailed description. The drawings show illustrations in accordance with exemplary embodiments. These exemplary embodiments, which are also referred to herein as "examples," are described in enough detail to enable those skilled in the art to practice the present subject matter. The embodiments can be combined, other embodiments can be utilized, or structural, logical and electrical changes can be made without departing from the scope of what is claimed. The following detailed description is, therefore, not to be taken in a limiting sense, and the scope is defined by the appended claims and their equivalents.

The present disclosure provides systems and methods for providing EWS of a health status of a patient. The patient may suffer from chronic diseases. Embodiments of the present disclosure can allow measuring medical parameters of a patient in a non-intrusive manner while, for example, the patient is at home, at work, outdoors, traveling, and at other stationary or mobile environments. Some example embodiments can provide for a wearable device (e.g., a wristband, a watch, or a bracelet) that includes sensors configured to measure medical parameters such as, for example, blood pressure, heart rate, blood oxygen saturation, respiration, and the like. The measurements can be taken during daytime and nighttime for days, weeks, months, and years. The medical parameters can be analyzed to determine trends in the medical parameters and an EWS for health status of the patient. The EWS can be further used to determine whether the severity of the patient's chronic disease (e.g., a heart disease, diabetes, lung disease, and so on) worsens or improves. Embodiments of the present technology may facilitate a rapid reaction to provide an appropriate and timely treatment for the patient. The early treatment may allow taking timely measures to avoid worsening of the patient's condition to the point of requiring an emergency hospitalization and associated expensive medical treatment.

According to various example embodiments, a method for providing the EWS of a health status of a patient includes acquiring, during a predetermined time period, by at least one processor communicatively coupled to sensors integrated into a wearable device, initial values of medical parameters of a patient. The wearable device can be designed to be worn on a wrist of the patient. The method may include determining, by the at least one processor and based on the initial values, normal values of the medical parameters. The method may further include acquiring, by the at least one processor via the sensors and at a pre-determined frequency, further values of the medical parameters. The method may further allow determining, by the at least one processor and based on deviations of the further values from the normal values, individual scores for the medical parameters. The method may further include calculating, by the at least one processor and based on the individual scores, a general score. The method may further include determining, by the at least one processor and based at least on the general score, the health status of the patient.

Referring now to FIG. 1, an example system 100 for providing the EWS of a health status of a patient is shown. The system 100 includes at least a wearable device 110. The wearable device 110 includes sensors 120. In some embodiments, the wearable device 110 is worn by a patient 130, for example on a wrist, for an extended period of time. The wearable device 110 can be carried out as a watch, a bracelet, a wristband, and the like.

The wearable device 110 is operable to constantly collect, via sensors 120, sensor data from a patient 130. In some embodiments, based on the sensor data, the wearable device 110 is operable to obtain medical parameters associated with the patient 130. The medical parameters can be analyzed to obtain changes (trends) in medical parameters and the EWS of health status of the patient over time. Based on the changes and the EWS, one or more conclusions regarding severity of one or more chronic disease can be obtained. The wearable device 110 is operable to send messages regarding a current health status to the patient, a relative, a caretaker of the patient, or a doctor treating the patient. The patient 130 can be advised to see a doctor and/or take medicine. In some embodiments, the wearable device 110 analyzes the medical parameters to determine whether the patient has taken the medicine and to provide further advice to the patient.

In various embodiments, the system 100 may further include a mobile device 140. The mobile device 140 can be communicatively coupled to the wearable device 110. In various embodiments, the mobile device 140 is operable to communicate with the wearable device 110 via a wireless connection. The mobile device 140 can include a mobile phone, a smart phone, a phablet, a tablet computer, a notebook, and so forth. The mobile device 140 can be operable to receive the sensor data and medical parameters from the wearable device 110. In certain embodiments, the mobile device 140 is operable to perform analysis of the received sensor data and medical parameters to determine an EWS concerning the health status of the patient. The mobile device 140 can be further configured to provide, based at least on the EWS, a report regarding current health status to the patient 130. In various embodiments, the mobile device 140 runs one or more applications that provide, via a graphical display system, charts and graphics concerning medical parameters of the patient.

In some embodiments, the mobile device 140 is operable to determine the severity of a health status resulting from the chronic disease from which the patient suffers and provide the patient with advice to see a medical professional or to take medicine. An alert message regarding health status of the patient can be sent to a doctor, a relative, or caretaker of the patient.

In further embodiments, the system 100 may further include a cloud-based computing resource 150 (also referred to as a computing cloud). In some embodiments, the cloud-based computing resource 150 includes one or more server farms/clusters comprising a collection of computer servers and is co-located with network switches and/or routers. In certain embodiments, the mobile device 140 is communicatively coupled to the computing cloud 150. The mobile device 140 can be operable to send the sensor data and medical parameters to the computing cloud 150 for further analysis. The computing cloud 150 is operable to store historical data concerning patient health status including sensor data, medical parameters, and EWS collected over days, weeks, months, and years. The computing cloud 150 can be operable to run one or more applications and to provide reports regarding health status of the patient. A doctor 170 treating the patient may access the reports, for example via computing device 160, using the Internet or a secure network. In some embodiments, the results of the analysis of the medical parameters can be sent back to the mobile device 140.

The severity of the health status resulting from a chronic disease can be estimated by computing a deviation or divergence from normal medical parameters of one or more medical parameters being measured at the moment. The normal medical parameters can be specific to the patient 130 and can be derived based on historical data concerning the patient's health status recorded over an extended time period. If the deviation in the medical parameters becomes sufficiently large, the patient can be advised, via a message to the mobile device 140, to take medicine or contact a doctor. In some situations, when the deviation becomes substantial, an alert message can be sent by the mobile device 140 and/or the wearable device 110 to a relative, a doctor, or a caretaker of the patient.

It may be desirable for the patient to be assured that the current medical parameters are within an acceptable deviation of the normal medical parameters. For example, when the current medical parameters are normal, the wearable device 110 and/or mobile device 140 can be operable to periodically alert the patient using a pleasant sound. The signal can be provided, for example, every 30 minutes, once every hour, and the like. In certain embodiments, when the medical parameters are within normal values, the mobile device 140 may provide a text message assuring the patient of normal conditions. A haptic feedback component can be used to alert the patient to a health condition, to warn the patient about a specific event concerning treatment of a chronic disease, to remind the patient to take a medicine, if the patient has failed to take the medicine within a predetermined period of time, and so forth. The wearable device 110 may include a haptic feedback functionality for providing the patient with haptic feedback, for example, a tap-in device, to apply a force or vibration to skin of the patient. In further embodiments, the haptic alert can be provided by the mobile device 140. The mobile device can vibrate when the mobile device in a pocket of the patient or when the mobile device is located on a surface (e.g., a table).

Figure 2:
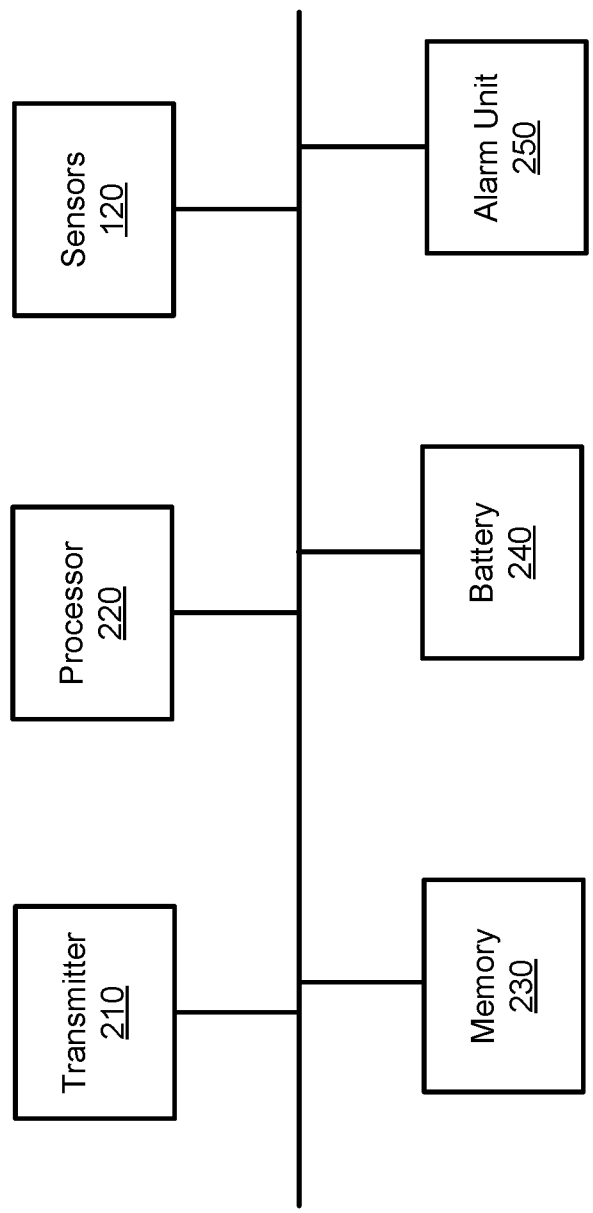
FIG. 2 is a block diagram showing components of an example device for providing EWS for a health status of a patient.

FIG. 2 is a block diagram illustrating components of a wearable device 110, according to an example embodiment. The example wearable device 110 includes sensors 120, a transmitter 210, processor 220, memory 230, a battery 240, and an alarm unit 250. The transmitter 210 is configured to communicate with a network such as the Internet, a Wide Area Network (WAN), a Local Area Network (LAN), a cellular network, and so forth, to send a data stream, for example sensor data, medical parameters, and messages concerning the health condition of a patient.

The processor 220 can include hardware and/or software, which is operable to execute computer programs stored in memory 230. The processor 220 can use floating point operations, complex operations, and other operations, including processing and analyzing sensor data to obtain current medical parameters and the EWS of the patient 130.

In some embodiments, the battery 240 is operable to provide electrical power for operation of other components of the wearable device 110. In some embodiments, the battery 240 is a rechargeable battery. In certain embodiments, the battery 240 is recharged using inductive charging technology.

In some embodiments, the alarm unit 250 may include a vibration unit, a tap-in device, a buzzer or a combination of thereof. The alarm unit 250 can be used to provide alarms to patient 130 by creating vibrational tactile sensations in pressure receptors of the skin of the patient or by playing sounds.

The wearable device 110 may comprise additional or different components to provide a particular operation or functionality. In some embodiments, the wearable device 110 may include one or more buttons (or touch screen elements) for entering information. For example, one of the buttons can be used to indicate that the patient is being supplied with external oxygen. In certain embodiments, one of the buttons can be used to enter a level of consciousness of the patient. In other embodiments, the wearable device 110 may include fewer components that perform similar or equivalent functions to those depicted in FIG. 2.

Figure 3:
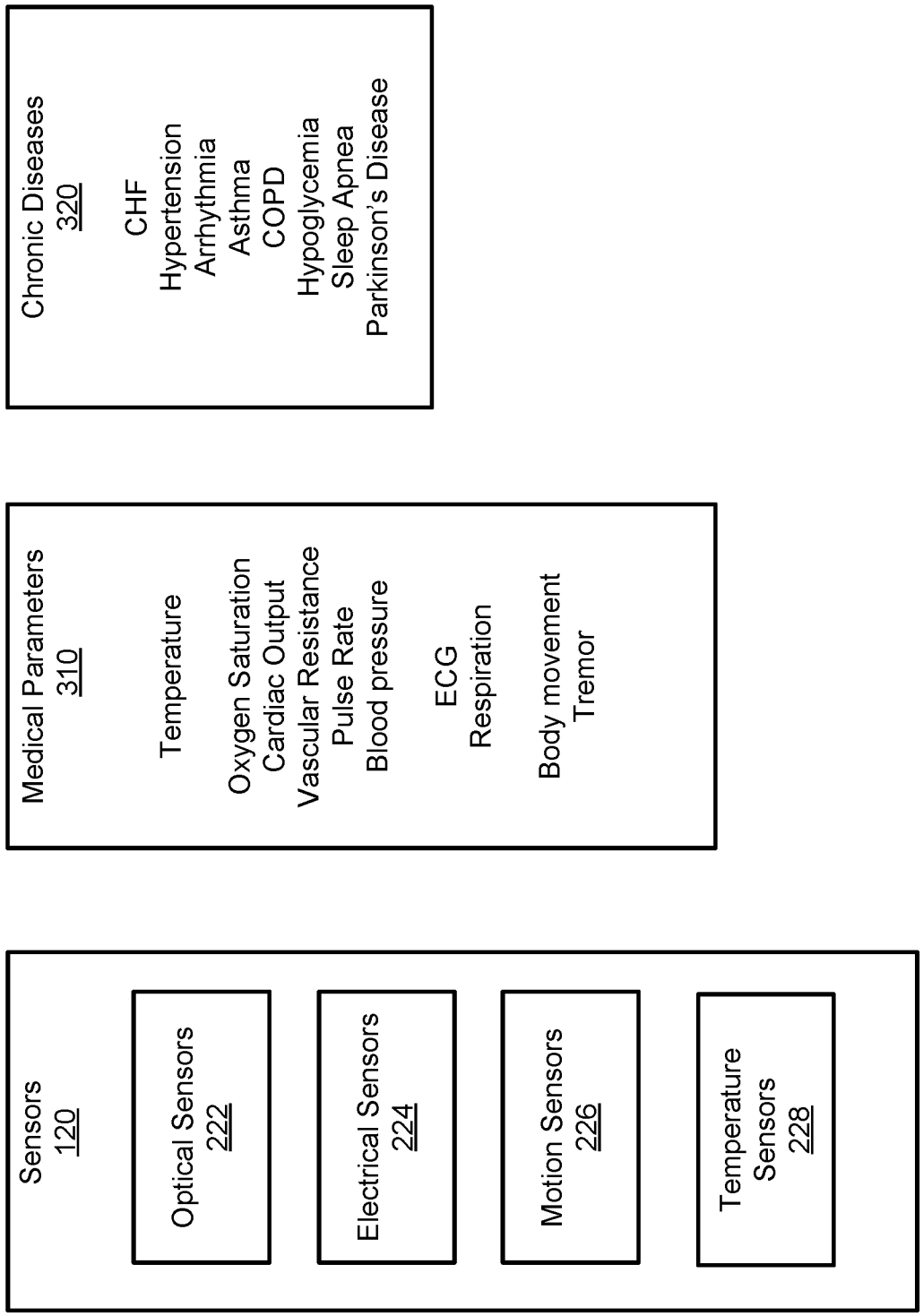
FIG. 3 is a block diagram illustrating example sensors, example medical parameters, and example chronic diseases.

FIG. 3 is a block diagram showing a plurality of example sensors 120, a plurality of example medical parameters 310, and a plurality of example chronic diseases 320. In various embodiments, the sensors 120 include optical sensors 222, electrical sensors 224, motion sensors 226, and temperature sensors 228. The medical parameters 310, determined based on the sensor data, include, but are not limited to, SpO2 oxygen saturation, tissue oxygen saturation, cardiac output, vascular resistance, pulse rate, blood pressure, respiration, electrocardiogram (ECG) data, and motion data. The chronic diseases 320, the progression of which can be tracked based on changes of the medical parameters, include but are not limited to congestive heart failure (CHF), hypertension, arrhythmia, asthma, chronic obstructive pulmonary disease (COPD), hypoglycemia, sleep apnea, and Parkinson's disease.

The optical sensors 222 are operable to measure medical parameters associated with blood flow in an artery (for example, radial artery) using changing absorbance of light at different wavelengths in arterial blood and skin. The optical sensors can determine multiple medical parameters, including but not limited to: SpO2 oxygen saturation, cardiac output, vascular resistance, pulse rate, and respiration. Based on the measurements obtained from optical sensors, abnormal cardiac rhythms (for example, atrial fibrillation, rapid rhythms and slow rhythms) can be detected.

In some embodiments, respiration can be derived from a sinus arrhythmia waveform. The sinus arrhythmia waveform can be obtained based on intervals between subsequent heart beats (RR intervals) measured by the optical sensors using the fact that the rhythm of the heart beats is modulated by human breathing.

The electrical sensors 224 can be operable to obtain electrocardiographic (ECG) activity data of the patient. The ECG activity data includes a characteristic electrically-derived waveform of a heart activity. The ECG data can include a number of components, whose characteristics (timing, amplitude, width, and so forth), alone or in combination, can provide a picture of cardiac and overall health. The ECG data is typically derived by measurements from one or more sets of leads (groups of electrodes comprising grounded circuits), such that the exact characteristics of the resulting waveforms is a function of the electrical and spatial vectors of the electrode positions relative to the heart. While the details of interpretation of the ECG data are too involved to describe succinctly in this disclosure, consideration of each of the component parameters can indicate health status, physical or psychological stress, or trends of disease conditions. Various cardiovascular parameters can be extracted from the ECG alone (such as a heart rate for example), or in combination with other physiological measurements.

ECG-like components can also be obtained, or re-constructed, through other methods of physiological measurements, such as mechano-cardiography, for example. According to example embodiments of present disclosure, ECG of the patient can be measured via the electrical sensors 224. Since measurements are taken from a wrist of the patient, electrodes (or input plates) of the electrical sensors 224 are located very close to each other on a wearable device 110. The electrodes can be positioned to constantly contact the skin of the patient 130 at least two points within a band of the skin surrounded by the wearable device 110. Therefore, the ECG data may contain noise. Averaging of several subsequent intervals of the ECG data between heart beats can be used to cancel out noise in ECG data. To determine intervals between two subsequent heart beats, the pulse wave as measured by optical sensors 222 can be used as a reference. In some embodiments, the pulse rate measured by the optical sensors 222 can be used as a reference signal to improve quality of ECG data of patient when the ECG data are measured from electrodes placed on two limbs (for example two wrists) of the patient. In certain embodiments, an arrhythmia analysis can be carried out using the ECG data and data concerning cardiac output and pulse rate.

In some embodiments, the motion sensors 226 include an accelerometer, gyroscope, and Inertial Measurement Unit (IMU). The motion data obtained via motion sensors 226 can provide parameters of body movement and tremor. The motion data can allow tracking the progression or remission of a motor disease, Parkinson's disease, and physical condition of the patient. In some embodiments, the motion data can be analyzed to determine whether the patient is likely to fall. In some embodiments, the motion data can be analyzed in time domain and frequency domain. By tracking amplitudes of movement of the patient it can be determined if the patient's movements become slower (i.e., the patient becomes sluggish) or the patient is not moving at all.

In some embodiments, the motion data obtained from the motion sensors 226 can be also used to obtain respiration data of the patient. For example, the motion sensors 226 may include a three-dimensional gyroscope. When the patient moves, the three-dimensional gyroscope can measure rotation around axes X, Y, and Z. The signal provided by the gyroscope may include components due to breathing of the patient. In some embodiments, the wearable device 110 can be configured to perform a spectral analysis on the signal provided by the three-dimensional gyroscope to determine a spectrum.

The signal may include rotation around one of the axes X, Y, Z, or a combination of the rotations. The spectrum analysis may include Fourier transform, periodogram-based methods, Bartlett's method, Welch's method, least-squares spectral analyses, and other techniques. The spectrum can be further used to determine a frequency of breathing (respiration). The respiration determined based on motion data may be more reliable than the respiration determined from a sinus arrhythmia waveform, since heart beat intervals measured by optical sensors can be contaminated if the patient suffers from a heart arrhythmia. The respiration measured by the wearable device can be also more reliable than manual counting of breathing carried out by medical personal.

FIG. 4A and FIG. 4B are schematic diagrams illustrating an example wearable device 110. In the examples of FIG. 4A and FIG. 4B, the wearable device 110 can be carried out in a shape of an open bangle. The FIG. 4A shows a top view of a patient's hand 410 and the wearable device 110 placed on the patient wrist. FIG. 4B is an inside view of the patient's hand 410 and wearable device 110. The wearable device 110 can be designed to apply pressure at an area 405 of skin surface covering a radial artery 420. In comparison to wristbands and straps, an open bangle may be more comfortable to wear by a patient since no pressure is applied to the middle area inside the wrist. It should be noted that sensors 120 (shown in FIG. 2) can be arranged around the wearable device HO to take appropriate measurements from the inside and top of the wrist of the patient.

The wearable device 110 can include optical sensors 222 located on an inner side of the wearable device 110. When the wearable device 110 is worn on the patient's hand, the inner side can be in permanent contact with a surface of the skin of the patient's hand 410. The wearable device 110 can be placed around a wrist of patient's hand 410 in such a way that optical sensors 222 are located as close as possible to cover the skin area 405 covering the radial artery 420. The optical sensors 222 can be configured to be in a permanent contact with the skin of the patient 130. The radial artery is located right beneath the skin, thereby allowing measurements of oxygen saturation, heart rate, cardiac output, and other parameters by optical sensors 222 using pulse oximetry methods.

Oxygen saturation is the relative proportion (typically expressed as percentage) of oxygen dissolved in blood, as bound to hemoglobin, relative to non-oxygen-bound hemoglobin. Oxygen saturation is important in clinical monitoring of surgical anesthesia, and in monitoring and assessment of various clinical conditions such as the COPD and asthma. In healthy individuals, oxygen saturation is over 95%. Direct measurement can be made from arterial blood sample, but drawing blood is an invasive procedure, and, except for a few controlled environments (e.g. during a surgery) cannot be easily performed continuously. Pulse oximetry can yield a quantity called SpO2 (saturation of peripheral oxygen), an accepted estimate of arterial oxygen saturation, derived from optical characteristics of blood using transmission of light through a thin part of a human body, for example, a fingertip or an earlobe (in the most common transmissive application mode). Reflectance pulse oximetry can be used to estimate SpO2 using other body sites. The reflectance pulse oximetry does not require a thin section of the person's body and is therefore can be suited to more universal application such as the feet, forehead and chest, but it has some serious issues due to the light reflected from non-pulsating tissues.

Figure 4C:
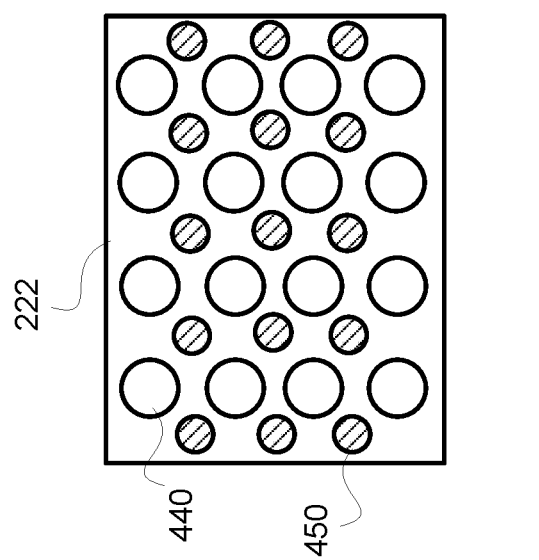
FIG. 4C is a block diagram showing an example optical sensor.

In other embodiments, as shown in FIG. 4C, the optical sensors 222 include multiple light sensors 440 (photoelectric cells), to measure the reflected light, and multiple light transmitters 450 (for example, Light Emission Diodes (LEDs)). The number and location of the light sensors and light transmitters can be chosen such that in case of an accidental displacement of the wearable device, at least one of the light sensors is still located sufficiently close to the radial artery. In some embodiments, when measuring the light reflected from the skin and radial artery, a signal from those photoelectric cells that provides the strongest or otherwise determined best output can be selected for further processing in order to obtain medical parameters using methods of pulse (reflectance) oximetry. In certain embodiments, the wearable device 110 is configured to apply a pre-determined amount of pressure to the wrist each time the user wears the wearable device to allow the same conditions for the reflection of the light from the skin.

In other embodiments, when oxygen saturation cannot be measured directly from arterial blood, an indirect measurement can be performed by tracking tissue oxygen saturation. The measurement of oxygen saturation is commonly used to track progression of heart diseases or lung disease. When heart or lungs are not functioning properly, the saturation of oxygen drops in both arterial blood and tissue around the artery. Therefore, tissue oxygen saturation can be measured by sensing the skin color near the radial artery. For example, if the wearable device 110 moves so that the optical sensors 222 are not covering the radial artery, measurements of tissue saturation near the radial artery can be used as a backup to provide values for oxygen saturation. In certain embodiments, the oxygen saturation and tissue saturation can be measured simultaneously. In some embodiments, the oxygen saturation and tissue saturation can be measured using the same optical sensor.

Referring now to FIG. 4A, the wearable device 110 may include input plates 415 and 417 of electrical sensors 224. The input plates 415 and 417 can be located on the inner side of the wearable device 110. When the wearable device 110 is placed on a wrist of the patient, the input plates 415 and 417 can be positioned to be in permanent contact with the skin of the wrist of the patient. In some embodiments, the input plates (electrodes) 415 and 417 shown can be configured to be located at the opposite edges of the wrist of patient.

In some embodiments, a combination of ECG and pulse oximetry can be used to determine cardiac output. Cardiac Output (CO, Q, or Qc) is a volume of blood pumped by the ventricles of the heart per unit time, typically expressed as milliliters per minute (ml/min). The cardiac output can be directly derived from other cardiac parameters, namely as the product of stroke volume (SV, the blood volume output of the heart with each beat), and the heart rate (HR), that is, CO=SV*HR. Clinically, the cardiac output is an indicator of the sufficiency of blood supply. In healthy individuals at rest, CO is about 5 or 6 liters of blood per minute. During strenuous activity, CO can increase to levels more than five times the resting level. In conditions such as hypertension, valvular heart disease, congenital heart disease, arrhythmias, CO is typically reduced.

In some embodiments, a combination of ECG and pulse oximetry can be used to estimate CO directly using the equation CO=SV*HR, by least squares regression modeling of stroke volume (based either on individual direct calibration to a specific patient, or calibration to physical and clinical patient characteristics), and replacing SV by the appropriate regression expression. Specifically, pulse wave transit time, the interval between the ECG R wave peak and the pulse oximeter pulse wave foot, transformed by an appropriate regression expression, replaces SV. The CO estimate can be determined using individual heartbeat raw ECG and pulse oximetry waveform parameters, or may be a time-averaged estimate, derived from synchronized reconstructed one-handed ECG and averaged pulse oximeter readings over a specified time period. Simple changes in CO, useful in tracking individualized patient trends, can be obtained by similar means, without the necessity for absolute calibration.

In some embodiments, the wearable device 110 is operable to determine a pulse rate. The pulse rate is an indicator of a heart rate, as determined at a peripheral body site (arteries of a wrist, arm, leg, or neck). Considered as one of the vital signs, the pulse rate can be an indicator of a general health and physiological state. The pulse rate can be derived directly from any pulse-oximeter. Normal resting values can vary widely, but typically, remain within 60-100 pulsations per minute. Fluctuations in the heart rate (Heart rate variability or HRV) are normal, with higher degrees generally associated with better heart reactivity and health.

In some embodiments, the wearable device 110 is operable to determine a blood pressure (BP). The BP, another vital sign, generally refers to the intra-arterial pressure of blood at two specific stages of the heartbeat, the maximum pressure at systole (ventricular contraction) and the minimum pressure at diastole (relaxation and filling of ventricles), expressed as a delimited pair of numbers for systolic and diastolic BP respectively, in mmHg, e.g. 150/80 mmHg. The BP can be measured continuously by an invasive arterial catheter, non-invasive measurement at the arm by a stethoscope and a sphygmomanometer, or an automated cuff. A healthy adult resting BP can vary around 120/80 mmHg. High or low BPs are associated with many disease states, with long-term changes being associated with changes in the health status. Extreme short-term changes can be associated with acute disease episodes, particularly in chronically ill patients. A risk of developing a number of diseases, such as cardiovascular disease, can be associated with extreme BPs. Short-term changes in the BP can be associated with changes in physical or mental state.

According to some embodiments of present disclosure, a combination of ECG and pulse oximetry can be used to estimate systolic BP changes. The systolic BP changes can be estimated using a pulse wave transit time, the interval between the ECG R wave peak and the pulse oximeter pulse wave foot.

In certain embodiments, with a suitable calibration and individualized adjustment based on various patient characteristics, absolute estimates of the BP can be determined. The BP changes or absolute estimates can be determined using individual heartbeat raw ECG and pulse oximetry waveform parameters, or may be a time-averaged estimate, derived from synchronized reconstructed one-handed ECG and averaged pulse oximeter readings over some specified time period.

In some embodiments, the wearable device 110 is operable to determine vascular resistance. Vascular resistance is the force which opposes the flow of blood through the circulation. Typically, the systemic vascular resistance (SVR), which is the resistance of the peripheral circulation, is considered. Measurements can be expressed in several different unit systems; clinically the units are often mmHg/L/min, as SVR is a function of both blood pressure and cardiac output, that is, SVR=BP/CO. Normal values are typically within 10-20 mmHg/L/min. SVR can change as a result of various physiological stresses on the body, such as with exercise where the vascular resistance decreases, resulting in increased blood flow, or with drug or disease-related challenges.

Using measurements of ECG and pulse oximetry, the SVR can be derived as either a change or tracking score, or an absolute estimate, based on instantaneous (single heartbeat) or average BP and CO estimates.

In some embodiments, the wearable device 110 is operable to determine respiratory rate using a pulse oximetry and ECG. The respiratory rate, which is another vital sign, is typically expressed as the number of breaths per minute. Typical adult resting respiratory rate is about 16-20 breaths per minute. Extreme variations can result from physical or psychological stress. The respiratory rate is often affected in chronic disease states, particularly in pulmonary and cardiovascular disease. Extreme short-term changes may be associated with acute disease episodes, particularly in chronically ill patients.

In some embodiments, the wearable device 110 may include a temperature sensor 425 and a temperature sensor 430. The temperature sensor 425 can be located on the inner side of the wearable device 110. When the wearable device 110 is worn on patient's hand, the temperature sensor 425 can be in permanent contact with the skin of the patient. The temperature sensor 425 can be used to measure temperature of the skin (a skin temperature) of the patient at the hand. In certain embodiments, the temperature sensor 425 can be located as close as possible to cover the skin area 405 covering the radial artery 420. Since the radial artery 420 carries blood coming from the core of the body of the patient, the temperature provided by the temperature sensor 425 may be close to core temperature of the patient. In some embodiments, the wearable device 110 may further include a temperature sensor 430. The temperature sensor 430 can be located at the outer side of the wearable device 110. The outer side is not in contact with the surface of the skin of the patient's hand. Therefore, the temperature sensor 430 can be used to measure a temperature of an external environment (an external temperature), for example, a temperature of air in a room.

In some embodiments, the wearable device 110 can be configured to estimate a body temperature of the patient based on measurements of the skin temperature and the external temperature. In some embodiments, the body temperature can be defined as a linear combination of the skin temperature and the external temperature. Coefficients of the linear combination can be determined by a calibration process using regular body temperature measurements. The calibration can be carried out at the first use of the wearable device 110 and periodically repeated during further uses of the wearable device. In other embodiments, the body temperature can be defined as a non-linear function of the skin temperature and the external temperature. Type and parameters of the non-linear function can be determined via the calibration process using regular body temperature measurements.

In further embodiments, the wearable device 110 can be operable to track levels of one or more medicine in the blood of the patient 130 for a desired period of time. The level of medicine can be analyzed in combination with other blood parameters to see trends in progression or regression of chronical diseases. Based on the trends, the patient can be provided with advice to modify times for taking the medicine and/or amounts of the medicine. The patient can be warned if the level of the medicine in the blood is too high or too low. The doctor 170 view reports on the medicine levels to ensure that the medication level is within a proper range for providing effective treatment of the chronic diseases.

In some embodiments, the wearable device 110 can facilitate monitoring trends of medical parameters of the patient during a treatment. The information concerning the trends can be further used to predict a reaction of the patient to various medicines.

In some embodiments, an analysis of trends of the medical parameters can be used to predict susceptibility of the patient to local environmental condition. For example, based on a weather forecast, a reaction of patient to a weather condition, pollen count, air pollution indices can be predicted. The patient can be given an advice, for example, to take a medicine in order to avoid worsening the health conditions.

In some embodiments, changes in monitored medical parameters can be correlated to certain social events, like news, or other external stimuli. The correlation can be used for determining psychological characteristics of the patient.

In some embodiments, the monitoring of medical parameters can be combined with monitoring particular habits of the patient. The habits can be determined based on movement activity. For example, the following can be monitored: a number of steps during a day, times of waking up and going to sleep, daily time periods of performing physical exercises, and so forth. Based on the changes in medical parameters, the user can be advised, for example to change quantity and/or quality of certain activities.

Figure 5:
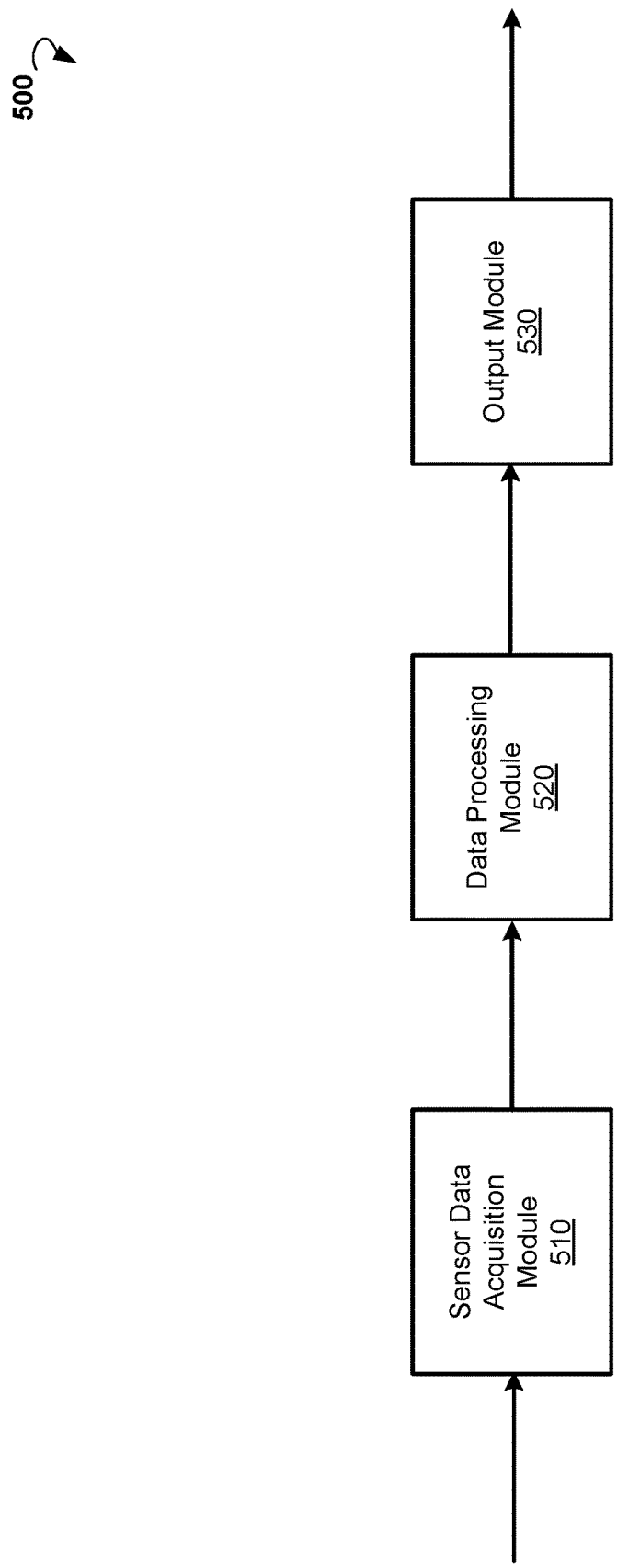
FIG. 5 is a block diagram showing an example system for providing EWS for a health status of a patient.

FIG. 5 is a block diagram showing components of system 500 for providing an EWS of a health status of a patient, according to an example embodiment. The system 500 can include a sensor data acquisition module 510, a data processing module 520, and output module 530. In some embodiments, the modules 510-530 are implemented as chipsets included in the wearable device 110. In other embodiments, the modules 520 and 530 can be stored as instructions in memory of the wearable device 110, mobile device 140, or computing cloud 150, and executed by a processor.

In some embodiments, the sensor data acquisition module 510 is configured to receive and digitalize the sensor data. The sensor data acquisition module 510 can include one or more analog-to-digital converters to transform the electrical signals from sensors to digits.

In some embodiments, the output module 530 can be configured to provide reports and alert messages concerning a health status of the patient 130.

In some embodiments, the data processing module 520 can be configured to analyze the sensor data to obtain medical parameters 310. The data processing module 520 can be configured to determine trends in the medical parameters 310 to track the health status of the patient 130. In certain embodiments, the data processing module 520 may be configured to determine a general score representing the health status of the patient. The general score can be a sum of individual scores of medical parameters being monitored while the wearable device 110 is in use. In some embodiments, the number of monitored medical parameters can be extended based on a current patient health status and environment conditions. In certain embodiments, the medical parameters can be assigned weights based on the current patient health status and environmental conditions. The weights can be used in a summation of the individual scores of the medical parameters.

In some embodiments, the monitored medical parameters may include at least a respiratory rate, an oxygen saturation, a temperature, a systolic blood pressure, a pulse rate, and a level of consciousness. In some embodiments, in order to determine the level of consciousness, the wearable device may be configured to provide a signal to the patient 130 by the alarm unit 250. The patient may be instructed to touch the wearable device 110 with the other hand. In some embodiments, the wearable device may include a touch sensor configured to sense whether the patient touched the wearable device. The level of consciousness can be determined based on whether the patient touched the wearable device after the wearable device provided a signal by the alarm unit 250.

In some embodiments, the data processing module 520 is configured to determine individual scores of the medical parameters. In certain embodiments, an individual score of a medical parameter is determined based on a deviation of a current value of the medical parameter from a normal value of the medical parameter. In some embodiments, the normal value of the medical parameter is unique to the patient 130. The normal value can be determined based on historical values of the medical In some embodiments, a range of possible values of the medical parameter is divided into intervals. Each of the intervals can be assigned a score. As a result, a scale or a table for determining an individual score of a patient, can be generated. The scores associated with the interval is zero if the interval is near the normal values of the medical parameters. The score of the interval may grow gradually up to a maximum value (for example, 3) with a deviation from the normal value on both sides of the normal value.

In some embodiments, the number of intervals and scores assigned to the intervals can be individual for the patient. In certain embodiments, the number of intervals and scores assigned to the intervals can be based on an age, a gender, a gene expression, and an ethnicity of the patient. In some embodiments, the number of intervals and scores assigned to the intervals can be based on a living environment of the patient. Thus, the scale of scores can be unique and individual to a given patient. Using a unique patient scale of scores may provide for a more precise evaluation of the general score as compared to scores generated based on normative values applicable to the population at large.

In some embodiments, the general score can be used to estimate a health status of patient. If the general score exceeds a pre-determined threshold, the patient can be issued a warning signal using, for example an alarm unit of the wearable device. In some embodiments, the warning signal can be also issued if one of the individual scores reaches a maximum value. The general score and the individual scores can be used for determining an appropriate treatment for the patient. In some embodiments, the general score can be used to determine or adjust a frequency for acquiring medical parameters and calculating individual scores.

Figure 6:
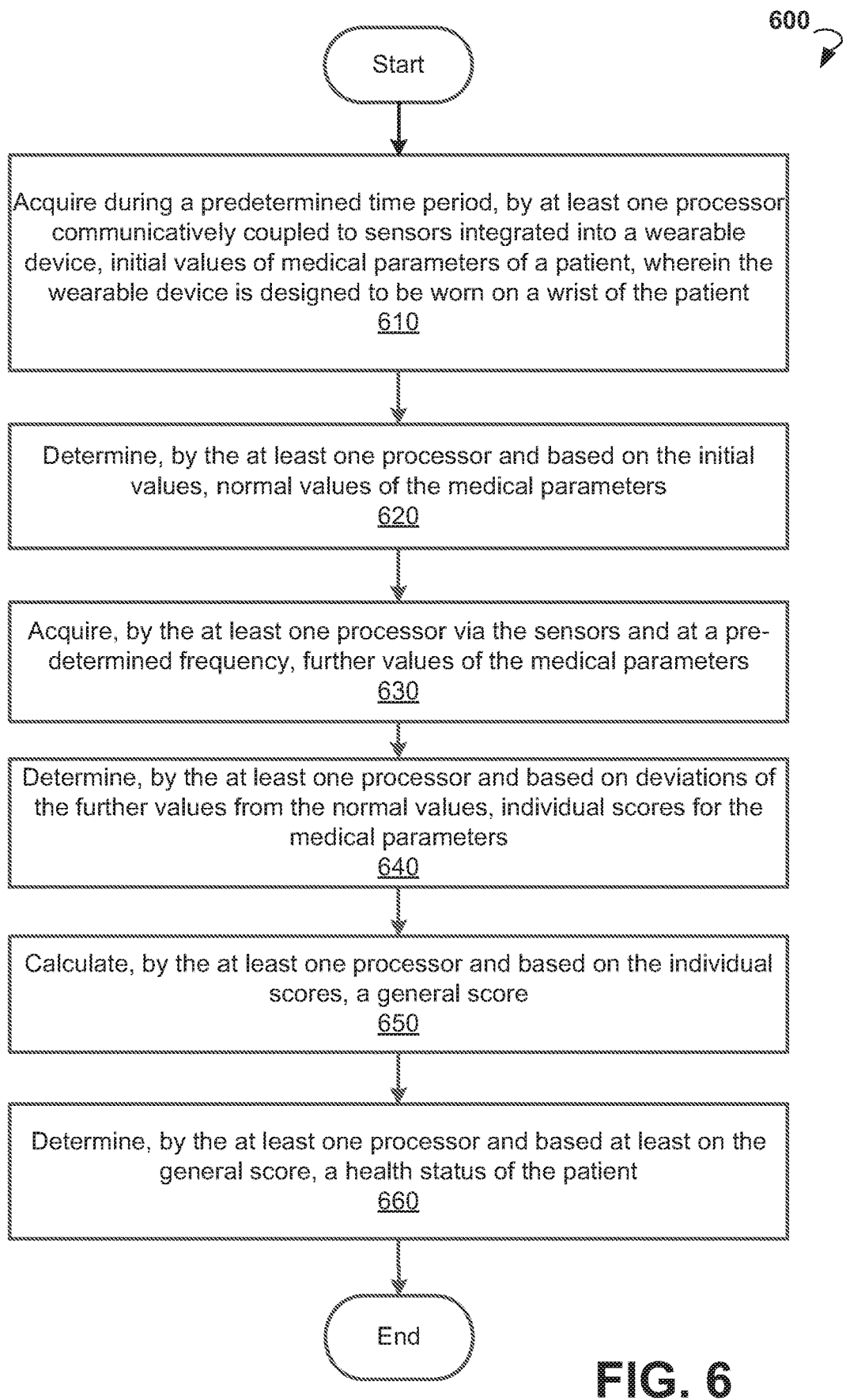
FIG. 6 is a flow chart showing steps of an example method for providing EWS for a health status of a patient.

FIG. 6 is a flow chart diagram showing example method 600 for early warning of health status of patient, according to an example embodiment.

In block 610, the method 600 includes acquiring, during a predetermined time period, by at least one processor communicatively coupled to sensors integrated into a wearable device, initial values of medical parameters of a patient. The wearable device can be designed to be worn on a wrist of the patient.

In block 620, the method 600 includes determining, by the at least one processor and based on the initial values, normal values of the medical parameters.

In block 630, the method 600 includes acquiring, by the at least one processor via the sensors and at a pre-determined frequency, further values of the medical parameters.

In block 640, the method 600 includes determining, by the at least one processor and based on deviations of the further values from the normal values, individual scores for the medical parameters.

In block 650, the method 600 includes calculating, by the at least one processor and based on the individual scores, a general score.

In block 660, the method 600 includes determining, by the at least one processor and based at least on the general score, the health status of the patient.

The present technology is described above with reference to example embodiments. Therefore, other variations upon the example embodiments are intended to be covered by the present disclosure.

What is claimed is:

1. A system for determining an early warning score for a health status of a patient, the system comprising:
    a set of sensors configured to continuously collect a plurality of medical parameters of the patient, the sensors being integrated into a wearable device, the wearable device being designed to be worn on a wrist of the patient, the sensors including at least a first temperature sensor configured to measure a skin temperature of a skin area over a radial artery of the patient and a second temperature sensor configured to measure an air temperature; and
    at least one processor communicatively coupled to the sensors, the at least one processor being configured to:
        acquire, via the sensors and during a pre-determined time period, initial values of the medical parameters, wherein the acquiring includes determining, based on the skin temperature and the air temperature, a body temperature of the patient;
        determine, based on the initial values, normal values of the medical parameters;
        acquire, via the sensors and at a pre-determined frequency, further values of the medical parameters;
        determine, based on deviations of the further values from the normal values, individual scores for the medical parameters;
        calculate, based on the individual scores, a general score indicative of the health status of the patient, wherein the calculating the general score includes multiplying the individual scores by weights to obtain weighted individual scores and summation of the weighted individual scores, the weights being based on a current health status of the patient and environmental conditions of the patient;
        determine, based at least on the general score, the health status of the patient, wherein the pre-determined frequency of acquiring the further values of the medical parameters and calculating the individual scores is adjusted based on the general score;
        divide a range of possible values of at least one of the medical parameters into intervals;
        assign each of the intervals a score; and
        based on the assigned scores of the intervals, generate a scale for determining the individual scores of the patient.

2. The system of claim 1, wherein determining the individual scores includes selecting decimal numbers assigned to pre-determined ranges of the medical parameters.

3. The system of claim 2, wherein the decimal numbers and the pre-determined ranges are based on at least one of a gender, an age, an ethnicity, a gene expression, and the environmental conditions of the patient.

4. The system of claim 2, wherein the decimal numbers and a number of the pre-determined ranges are individual to the patient.

5. The system of claim 1, wherein a number of the medical parameters is based on the environmental conditions of the patient.

6. The system of claim 1, wherein the at least one processor is further configured to adjust, based on the general score, a number of the medical parameters.

7. The system of claim 1, wherein the at least one processor is further configured to:
    determine that the general score exceeds a first pre-determined threshold; and
    based on the determination, issue an alarm regarding the health status of patient.

8. The system of claim 1, wherein the medical parameters include at least respiratory rate, an oxygen saturation, the body temperature, the skin temperature, a systolic blood pressure, a pulse rate, and a level of consciousness.

9. The system of claim 8, wherein:
    the wearable device includes an alarm unit and a touch sensor, the alarm unit and the touch sensor being communicatively coupled to the at least one processor; and
    the at least one processor is further configured to:
        enable the alarm unit to prompt the patient to touch the touch sensor on the wearable device;
        determine, via the touch sensor, whether the patient touched the touch sensor; and
        based on a result of the determination, evaluate the level of consciousness.

10. The system of claim 8, wherein:
    the wearable device includes at least one gyroscope configured to provide motion data;
and wherein the at least one processor is further configured to:
    analyze the motion data to obtain a spectrum; and
    determine, based on the spectrum, the respiratory rate.

11. The system of claim 8, wherein the at least one processor is further configured to:
    determine that an individual score of the individual scores exceeds a pre-determined threshold; and
    based on the determination, issue an alarm regarding the health status of patient.

12. A method for determining an early warning score for a health status of a patient, the method comprising:
    acquiring, during a pre-determined time period, by at least one processor communicatively coupled to sensors integrated into a wearable device, initial values of medical parameters of a patient, the wearable device being designed to be worn on a wrist of the patient, the sensors including at least a first temperature sensor configured to measure a skin temperature of a skin area over a radial artery of the patient and a second temperature sensor configured to measure an air temperature, wherein the acquiring includes determining, based on the skin temperature and the air temperature, a body temperature of the patient;
    determining, by the at least one processor and based on the initial values, normal values of the medical parameters;
    acquiring, by the at least one processor via the sensors and at a pre-determined frequency, further values of the medical parameters;
    determining, by the at least one processor and based on deviations of the further values from the normal values, individual scores for the medical parameters;
    calculating, by the at least one processor and based on the individual scores, a general score indicative of the health status of the patient, wherein the calculating the general score includes multiplying the individual scores by weights to obtain weighted individual scores and summation of the weighted individual scores, the weights being based on a current health status of the patient and environmental conditions of the patient;
    determining, by the at least one processor and based at least on the general score, the health status of the patient, wherein the pre-determined frequency of acquiring the further values of the medical parameters and calculating the individual scores is adjusted based on the general score;

dividing a range of possible values of at least one of the medical parameters into intervals;

assigning each of the intervals a score; and based on the assigned scores of the intervals, generating a scale for determining the individual scores of the patient.

13. The method of claim 12, wherein the determining of the individual scores includes selecting decimal numbers assigned to pre-determined ranges of the medical parameters.

14. The method of claim 13, wherein the decimal numbers and the pre-determined ranges are based on at least one of a gender, an age, an ethnicity, a gene expression, and the environmental conditions of the patient.

15. The method of claim 13, wherein the decimal numbers and a number of the pre-determined ranges are individual to the patient.

16. The method of claim 12, wherein a number of the medical parameters is based on the environmental conditions of the patient.

17. The method of claim 12, further comprising adjusting, by the at least one processor and based on the general score, a number of the medical parameters.

18. The method of claim 12, further comprising:

determining, by the at least one processor, that the general score exceeds a first pre-determined threshold; and based on the determination, issuing, by the at least one processor, an alarm regarding the health status of patient.

19. The method of claim 12, wherein the medical parameters include at least respiratory rate, an oxygen saturation, the body temperature, the skin temperature, a systolic blood pressure, a pulse rate, and a level of consciousness.

20. The method of claim 19, further comprising:

enabling, by the at least one processor, an alarm unit to prompt the patient to touch a touch sensor on the wearable device, the alarm unit and the touch sensor being communicatively coupled to the at least one processor, the alarm unit being integrated into the wearable device;

determining, via the touch sensor, whether the patient touched the touch sensor; and based the determination, evaluate the level of consciousness.

21. A non-transitory computer-readable storage medium having embodied thereon instructions, which when executed by at least one processor, perform steps of a method for determining an early warning score for a health status of a patient, the method comprising:

acquiring during a pre-determined time period, via sensors integrated into a wearable device, initial values of medical parameters of patient, wherein the wearable device is designed to be worn on a wrist of the patient, the sensors including at least a first temperature sensor configured to measure a skin temperature of a skin area over a radial artery of the patient and a second temperature sensor configured to measure an air temperature, wherein the acquiring includes determining, based on the skin temperature and the air temperature, a body temperature of the patient;

determining, based on the initial values, normal values of the medical parameters;

acquiring, via the sensors and at a pre-determined frequency, further values of the medical parameters;

determining, based on deviations of the further values from the normal values, individual scores for the medical parameters;

calculating based on the individual scores, a general score indicative of the health status of the patient, wherein the calculating the general score includes multiplying the individual scores by weights to obtain weighted individual scores and summation of the weighted individual scores, the weights being based on a current health status of the patient and environmental conditions of the patient;

determining, based at least on the general score, the health status of the patient, wherein the pre-determined frequency of acquiring the further values of the medical parameters and calculating the individual scores is adjusted based on the general score;

dividing a range of possible values of at least one of the medical parameters into intervals;

assigning each of the intervals a score; and based on the assigned scores of the intervals, generating a scale for determining the individual scores of the patient.

22. The method of claim 12, wherein a number of intervals, the scores assigned to the intervals, and the scale are unique and individual for the patient, based on one of a gender, an age, an ethnicity, a gene expression, and the environmental conditions of the patient.

23. The system of claim 1, wherein a number of intervals, the scores assigned to the intervals, and the scale are unique and individual for the patient, based on one of a gender, an age, an ethnicity, a gene expression, and the environmental conditions of the patient.

24. The non-transitory computer-readable storage medium of claim 21, wherein a number of intervals, the scores assigned to the intervals, and the scale are unique and individual for the patient, based on one of a gender, an age, an ethnicity, a gene expression, and the environmental conditions of the patient.

* * * * *